United States Patent [19]

Matros et al.

[11] Patent Number: 4,908,390
[45] Date of Patent: Mar. 13, 1990

[54] METHOD OF PREPARING METHANOL

[75] Inventors: Jury S. Matros; Ilya A. Zolotarsky, both of Novosibirsk, U.S.S.R.

[73] Assignee: Akademii Institut Katalizsa Sibirskogo Otdelenia Nauk SSSR, Novosibirsk, U.S.S.R.

[21] Appl. No.: 240,235

[22] PCT Filed: Oct. 14, 1987

[86] PCT No.: PCT/SU87/00112
§ 371 Date: Jun. 7, 1988
§ 102(e) Date: Jun. 7, 1988

[87] PCT Pub. No.: WO88/02744
PCT Pub. Date: Apr. 21, 1988

[30] Foreign Application Priority Data

Oct. 17, 1986 [SU] U.S.S.R. .............................. 4131462

[51] Int. Cl.$^4$ ............................................. C07C 27/06
[52] U.S. Cl. ..................................... 518/706; 518/713
[58] Field of Search .......................................... 518/706

[56] References Cited

FOREIGN PATENT DOCUMENTS 1249010  8/1987  U.S.S.R. .

*Primary Examiner*—Howard T. Mars
*Attorney, Agent, or Firm*—Ladas & Parry

[57] ABSTRACT

A method of preparing methanol consists in that a synthesis-gas containing carbon oxides and hyddrogen is passed through a fixed bed of a copper-containing catalyst under pressure of 3.0–15.0 MPa at a temperature of from 150° to 300° C. The catalyst is divided into two parts either in an equal proportion or in a smaller/greater ratio equal to 0.5–1. The gaseous mixture obtained after passing the first part of the catalyst bed is stirred prior to the supply thereof to the second part of the catalyst bed. As a result, the reaction mixture is formed containing the aim product. Each subsequent direction of passing the synthesis-gas through the catalyst bed and that of removing the reaction mixture are changed to opposite with respect to the previous direction.

2 Claims, No Drawings

METHOD OF PREPARING METHANOL

FIELD OF THE ART

The present invention relates to methods of synthesizing methanol from synthesis-gas containing carbon oxides and hydrogen on plants of chemical, petrochemical and other industries.

PRIOR ART

Methanol is used for production of formaldehyde, acetic acid, various esters, alkylhalides, synthetic protein, gasoline, numerous dyes, pharmaceutical preparations, fragrant and other compounds, and is employed as a solvent.

In the known most promising methods of methanol synthesis, the processes are, as a rule, performed under pressure 3-15 MPa at temperatures from 150° to 300° C. by passing synthesis-gas containing carbon oxides and hydrogen over copper-containing catalysts characterized by high activity and selectivity. Methanol is prepared from carbon oxides and hydrogen by following the reactions $$CO + 2H_2 \rightleftharpoons CH_3OH + 23.8 \text{ kcal/mol},$$

$$CO_2 + 3H_3 \rightleftharpoons CH_3OH + H_2O + 14 \text{ kcal/mol}.$$

Due to the fact that the reactions of methanol synthesis are exothermal and reversible, a maximum yield of methanol is attained within a theoretically optimum temperature range which is characterized by a constant decrease in temperature with increasing methanol concentration.

In the known methods of methanol synthesis the attempts are made to work under theoretically optimum conditions since at temperatures above 300° C. an accelerated deactivation of copper-containing catalysts takes place.

To enhance the degree of conversion of the initial raw material and prevent overheating of the catalyst, the process of methanol synthesis is usually carried out with a recycle. The reaction products are separated from the reaction mixture formed after passing synthesis-gas through a reactor. A part of the reaction mixture is directed to constant blowing-off and the rest part is mixed with a fresh portion of synthesis-gas and returned to the reactor input.

Known in the art are methods of methanol synthesis performed in reactors with a fixed catalyst bed operating under stationary (GB, 1484367) or artificially attained non-stationary (SU, A, 1249010) conditions.

To attain theoretically optimum conditions in the reactors operating under stationary conditions the control over a temperature regime is performed either by recuperative heat removal both from the whole catalyst bed and from the separate parts thereof, or by the addition of cold synthesis-gas. The synthesis-gas is heated to the initial temperature of the reaction (150°-240° C.) with the aid of recuperative heat exchangers.

In the reactors with heat removal from the whole catalyst bed said catalyst is placed either inside the tubes surrounded with a cooling agent or in the intertube space with a cooling agent inside the tubes. This method is characterized by complex equipment, high metal content of the reactor, and insufficiently high degree of conversion of synthesis-gas into methanol.

In the reactors with intermediate cooling the catalyst is placed in several (usually 3-5) adiabatically operating beds between which either heat is removed with the aid of any coolant or mixing of the reaction mixture with cooled synthesis-gas is performed. In this method of methanol synthesis with an intermediate cooling it is impossible to realize temperature regimes close to theoretically optimum ones which results in insufficiently high degrees of conversion of the synthesis-gas into methanol. In addition, the method is characterized by bulky equipment and high metal content of methanol production.

Also known in the art is a method of preparing methanol performed under artificially attained non-stationary conditions when synthesis-gas is heated to the initial reaction temperature not by recuperative but regenerative heat exchange via a period change (in 1-30 min) of every subsequent direction of the synthesis-gas flow through a catalyst bed and of the reaction mixture removal to the opposite one. In this case the catalyst bed itself plays a role of a regenerative heat exchanger.

According to the above method, methanol synthesis is carried out in a reactor containing one adiabatically operating bed of copper-containing catalyst along the faces of which grainy beds of inert material can be placed. Prior to operation the catalyst is heated to the initial temperature of the reaction (150°-240° C.) with the aid of a starting heat exchanger or electric heater. Then synthesis-gas is fed onto the heated catalyst at a temperature of 20°-170° C. Upon passing the synthesis-gas through a stationary catalyst bed at 150°-300° C., the reaction mixture containing the aim product is formed and removed from the catalyst bed. At a half-cycle period (1-30 min) the direction of the synthesis-gas supply is changed to the opposite one with the aid of a switching device.

Thus, changing every 1-30 min the subsequent direction of passing synthesis-gas through the catalyst bed and of removing the reaction mixture to the opposite one with respect to the previous direction, i.e. interchanging periodically the positions of the synthesis-gas input to the catalyst bed and of the reaction mixture removal, one performs a continuous process of methanol synthesis under non-stationary conditions. Under such conditions the temperature regime is realized which is characterized by three zones: a zone of heating synthesis-gas where temperature rises along the catalyst bed, a zone of high temperatures in the centre of the catalyst bed, and a zone where the catalyst temperature decreases with increasing concentration of methanol in the reaction mixture. The third zone of the temperature regime arises due to thermal inertia of the catalyst cooled by the synthesis-gas in the course of the previous semi-cycle. The described temperature regime is close to theoretically optimum and allows one to attain sufficiently high degrees of conversion of the initial synthesis-gas into methanol in one catalyst bed without intermediate or constant cooling of the reaction mixture with the aid of recuperative heat removal or by-pass valves for cold synthesis-gas.

The absence of the devices for cooling the reaction mixture and of recuperative heat-exchangers for heating synthesis-gas up to the initial temperature of the reaction as well as high output ensure high efficiency of the described process.

A non-stationary method of methanol synthesis is characterized by a considerable sensitivity of the temperature regime in the reactor to space structural inhomogeneity of the fixed catalyst bed and to heat losses through the reaction wall which is always the case in practice. Due to structural inhomogeneities in each cross-section of the catalyst bed perpendicular to the direction of the reaction mixture, the catalyst areas appear with strongly different temperatures. This means that in each cross-section of the bed there are areas with local overheating of the catalyst and areas with lower temperature. The temperature difference can be more than 70° C. Such areas prevent the operation in the optimum temperature regime over the whole bulk of the catalyst bed thereby adversely affecting the methanol yield and the catalyst service life.

DISCLOSURE OF THE INVENTION

It is an object of the invention to modify the process conditions in a method of preparing methanol, so as to enhance the output of the process and the service life of the catalyst.

In accordance with this and other objects, the invention consists in that a method is proposed of preparing methanol from synthesis-gas containing carbon oxides and hydrogen by passing said synthesis-gas through a fixed bed of copper-containing catalyst at temperatures of 150°–300° C. under pressure of 3–15 MPa with the formation of the reaction mixture containing the desired product, each subsequent direction of the synthesis-gas passing through the catalyst bed and of the reaction mixture removal being changed to the opposite one with respect to the previous direction; the method in which, according to the invention, the catalyst bed is divided into two parts either equal or with a smaller/greater volume ratio equal to 0.5–1 and the gaseous mixture obtained after passing the first part of the catalyst bed is stirred prior to the delivery to the second part of the bed.

Synthesis-gas containing carbon oxides and hydrogen can be obtained by processing liquid, solid or gaseous hydrocarbon raw material by any known methods. Besides, use can be made of synthesis-gas which is a waste product of some chemical production for instance, blowing-off gases in methanol production.

Highly active copper-containing catalysts of methanol synthesis contain, in addition to copper, zinc oxide and one or several other oxides. Methanol synthesis on such catalysts is performed under pressure of 3–15 MPa. Under such pressure the reactions proceed with a noticeable rate at temperatures above 150° C. Since thermal stability of the catalyst is limited, the temperature of the process must not exceed 300° C.

The presence of areas with strongly different temperatures of the catalyst in one cross-section of the catalyst bed may be due to inhomogeneities of the catalyst bed caused by way of charging, accumulation of catalyst dust, different activities of catalyst batches, nonuniform packing of the bed, and by the effect of the reactor wall. Prior to the accomplishment of the non-stationary process of methanol synthesis, the catalyst bed is heated uniformly. When the method without stirring the gaseous mixture is realized, the areas with strongly different temperatures of the catalyst in the cross-section of the catalyst bed perpendicular to the direction of the gaseous mixture flow arise at some time after the beginning of supply of a cold synthesis-gas to a preliminary heated catalyst bed. This time period is much greater than that between changes of the directions of the synthesis-gas flow. Therefore, in non-stationary process with stirring the gaseous mixture the time period between the supplies is insufficient for the formation of catalyst areas with strongly different temperatures during a semi-cycle between the changes of the directions and in the next semi-cycle, when the direction is opposite, the areas formed are destroyed but new areas appear which are destroyed during the next semi-cycle, and so on. The areas are destroyed the faster, the higher is the temperature of the stirred gaseous mixture. Thus, the stirring of the gaseous mixture is most efficient when it is performed in the zone of maximum temperatures. Therefore, it is expedient to divide the catalyst bed either in an equal proportion or in a smaller/greater volume ratio equal to 0.5–1, i.e. in the zone of maximum temperatures.

The gaseous mixture can be stirred with different intensity. The stirring is optimum when it ensures the temperature gradient in the flow of the gaseous mixture at the input to the second part of the catalyst bed no more than 150° C.

Realization of the proposed method makes it possible to eliminate the areas of the catalyst bed with strongly different temperatures in one cross-section of the catalyst bed which ensures a more optimum temperature regime in the whole bulk of the catalyst bed.

This enhances the output of the process of methanol synthesis when operation is performed without recirculation of the reaction mixture by 10–30 %.

BEST WAY OF CARRYING OUT THE INVENTION INTO EFFECT

The herein-proposed method of preparing methanol is technologically simple and is accomplished in the following way.

Prior to putting in operation a reactor for synthesis, a catalyst bed is heated to 180°–280° C. by any known method, for instance, by a nitrogen or synthesis-gas flow with the aid of a starting electric heater or heat exchanger. Then the synthesis-gas containing carbon oxides and hydrogen is continuously passed at 20°–170° C. under pressure of 3–15 MPa through the first part of the fixed bed of a copper-containing catalyst where the synthesis-gas is heated by heat of the catalyst to the initial temperature of the reaction. This is accompanied by cooling the corresponding area of the catalyst bed. When the synthesis-gas is passed through the catalyst bed at a temperature of 150°–300° C., the gaseous mixture containing methanol is formed.

The gaseous mixture obtained after passing the first part of the catalyst bed is stirred by the known method. Then the gaseous mixture is fed to the second part of the fixed bed of copper-containing catalyst where a methanol content in the gaseous mixture is further increased. The reaction mixture formed after pasing the whole catalyst bed is removed from the reactor and subjected to separation of methanol by any known method.

At a semi-cycle period equal to 1–30 min the direction of passing the synthesis-gas through the catalyst bed and that of removing the reaction mixture are changed to opposite with the aid of two three-run or four-run switching devices. The synthesis-gas with a temperature of 20°–170° C. is fed to the first (previously second) heated part of the catalyst bed from the face of the bed wherefrom the reaction mixture was removed during the previous semi-cycle. Due to heat of the catalyst, the synthesis-gas is heated to the initial temperature of the reaction after which a methanol-containing gaseous mixture is formed at 150°–300° C. The gaseous mixture leaving the first part of the catalyst bed is stirred by the same method as in the previous semi-cycle and fed to the second (previously first) part of the catalyst bed. The reaction mixture is removed from the reactor and processed for isolation of methanol.

At a semi-cycle period equal to 1–30 min the direction of passing the synthesis-gas through the catalyst bed and that of removing the reaction mixture are changed again to opposite.

Thus, the process is carried out continuously with the direction of filtration of the synthesis-gas through the fixed catalyst bed being changed to opposite every 1–30 min.

With the use of the above-described catalysts of different activities the process is performed at space velocities of the gas 2000–15000 $h^{-1}$, usually 5000–10000 $h^{-1}$.

The catalyst bed is divided into two parts either in an equal proportion or in a smaller/greater ration equal to 0.5–1, the gaseous mixture being stirred between these parts.

The catalyst bed can be placed both in one column of synthesis and in two columns. In the second case no special devices for stirring the gaseous mixture are required since the mixture is stirred sufficiently well in a tube connecting both parts of the bed.

When both parts of the catalyst bed are placed in one column various technical solutions can be realized. For instance, the gaseous mixture can be stirred with the aid of a double segmentized grate.

For a better understanding of the present invention specific examples are given hereinbelow by way of illustration.

EXAMPLE 1

A synthesis-gas (14400 $nm^3/h$) containing (vol. %) CO -3, $CO_2$ - 2, $H_2$ - 82, $N_2$ - 1.7, $CH_4$ - 10.9, $CH_3OH$ - 0.4 and $H_2O$ - 0.02 is delivered for methanol synthesis under pressure 7.2 MPa at 40° C. A copper-zinc-aluminium catalyst (2 tons is loaded into a reactor for synthesis. The catalyst bed is divided into two equal parts each of which is located on a separate distribution grate. The parts of the catalyst bed are separated by a blank partition with a tube through which the gaseous mixture is delivered from one part of the catalyst bed into the other.

Prior to start, the catalyst is heated with a nitrogen gaseous flow heated to 250° C. with the aid of a starting electric heater.

Then synthesis-gas heated to 40° C. is fed into the first part of the catalyst bed. The gaseous mixture obtained after passing the first part of the catalyst bed is directed to the tube connecting two parts of the catalyst bed where it is stirred in a turbulent flow.

The stirred gaseous mixture is passed through the second part of the catalyst bed. The reaction mixture obtained at the output of the second part of the catalyst bed is removed from the reactor and directed for isolation of the products.

In 5 min the direction of passing the synthesis-gas and that of removing the reaction mixture are changed to opposite with the aid of a four-run switchers. The initial synthesis-gas with a temperature of 40° C. is supplied to the first (previously second) part of the catalyst bed from the face of the bed wherefrom the reaction mixture was removed in the previous semi-cycle. The gaseous mixture obtained after passing the first part of the catalyst bed is stirred in the previous semi-cycle and fed into the second (previously first) part of the catalyst bed. The reaction mixture is removed from the reactor and directed for isolation of the reactions products.

In 5 min the direction of passing the synthesis-gas through the catalyst bed and that of removing the reaction mixture are changed again.

Thus, the process is performed continuously by changing every 5 min the direction of filtration of the synthesis-gas through the fixed bed of the catalyst.

After six switchings a periodic temperature regime is attained in the reactor. The reaction mixture with an average methanol concentration of 4.2 vol % is cooled and directed to a separator for isolating raw methanol. An average output of the catalyst is 11.3 $t/m^3$ day and maximum temperature is 278° C.

EXAMPLE 2

Methanol synthesis is performed as described in Example 1 but the amount of the catalyst loaded into the reactor is 2 tons and the catalyst bed is divided into two parts with a smaller/greater ratio of 0.5.

An average methanol concentration at the output of the reactor is 3.9 vol. %. An average output of the catalyst is 10.5 $t/m^3$ day and maximum temperature in the reactor is 285° C.

EXAMPLE 3

Methanol synthesis is performed as described in Example 1 but synthesis-gas is delivered into the reactor under pressure of 3 MPa. The process is performed with changing the direction of synthesis-gas filtration every 7 min.

An average methanol concentration at the reactor output is 2.8 vol. %. An average output is 7.3 $t/m^3$ day and maximum temperature of the reactor is 265° C.

EXAMPLE 4

Synthesis-gas (15000 $nm^3/h$) of the composition (vol. %) CO - 3, $CO_2$ - 2, $H_2$ - 82.2, $N_2$ - 1.7, $CH_4$ - 10.9, $CH_3OH$ - 0.2, $H_2O$ - 0.01 is delivered for methanol synthesis under 15 MPa at 40° C. The catalyst bed is divided into two parts with a smaller/greater ratio equal to 0.8. Each part of the catalyst bed is located in a separate column. The columns are connected with a tube. Copper-zinc-chromium catalyst is loaded in amounts 1.1 tons into one of the column and 1.4 tons into the second column.

Prior to start both columns are heated with a nitrogen flow having the temperature of 230° C. with the aid of a starting electric heater.

Then synthesis-gas with a temperature of 40° C. is fed into the bottom of the column with a greater catalyst amount. The gaseous mixture obtained after passing the first part of the catalyst bed is removed from the upper part of the column and supplied to the tube where the mixture is stirred and delivered to the upper part of the second column. The stirred gaseous mixture is passed through the second part of the column in the downward direction. The reaction mixture obtained at the output of the second part of the catalyst bed is removed from the bottom of the column and directed for isolation of the products.

Every 3 min the direction of passing the synthesis-gas through the catalyst bed and that of removing the reaction mixture are changed to opposite with the aid of two three-run valves. The initial synthesis-gas with a temperature of 40° C. is fed into the bottom of the column with a smaller amount of the catalyst. The gaseous mixture obtained after passing the first (previously second) part of the catalyst bed in the upward direction is removed from the column, stirred in the tube, and delivered to the upper part of the second (previously first) column. The reaction mixture is removed from the bottom of the second column and directed for isolation of the reaction products.

In 3 min the directions of passing the synthesis-gas through the catalyst bed and removing the reaction mixture are changed again to opposite. Thus, the process is carried out continuously with a change of the direction of synthesis-gas filtration through the fixed catalyst bed to opposite every 3 min.

After 15 switchings a periodic temperature regime is attained in the columns. The reaction mixture with an average methanol concentration of 4.9 vol. % is cooled and directed to a separator for isolating raw methanol. An average output of the catalyst is 13.8 t/m$^3$ day and maximum temperature of the catalyst bed is 300° C.

Industrial Applicability

The herein-proposed method may find application in the chemical and petrochemical industries at newly organized and reconstructed methanol-producing enterprises.

We claim:
1. A method of preparing methanol from a synthesis-gas containing carbon oxides and hydrogen by passing the synthesis-gas through a stationary bed of a copper-containing catalyst at a temperature of 150°–300° C. and a pressure of 3.0–15.0 MPa with the formation of a reaction mixture containing the desired product, the direction of each subsequent passage of the synthesis-gas through the catalyst bed and the direction of the removal of the reaction mass being reversed with respect to the preceding one, characterized in that the catalyst bed is divided into two parts either in an equal volume ratio or in the minor/major volume ratio equal to 0.5–1, the gas mixture resulting after passing the first part of the catalyst bed being stirred before supplying it to the second part of the catalyst bed.

2. A method according to claim 1, characterized in that stirring of the gas mixture is performed until the temperature gradient in the flow of the gas mixture at the inlet to the second part of the catalyst bed is no more than 15° C.

* * * * *